United States Patent
Bahl et al.

(10) Patent No.: US 10,234,444 B2
(45) Date of Patent: Mar. 19, 2019

(54) SYSTEM AND METHOD FOR NANO-OPTO-MECHANICAL-FLUIDIC SENSING OF PARTICLES

(71) Applicant: The Board of Trustees of the University of Illinois, Urbana, IL (US)

(72) Inventors: Gaurav Bahl, Champaign, IL (US); Kewen Han, Champaign, IL (US)

(73) Assignee: The Board of Trustees of the University of Illinois, Urbana, IL (US)

(*) Notice: Subject to any disclaimer, the term of this patent is extended or adjusted under 35 U.S.C. 154(b) by 251 days.

(21) Appl. No.: 15/278,633

(22) Filed: Sep. 28, 2016

(65) Prior Publication Data

US 2017/0089819 A1    Mar. 30, 2017

Related U.S. Application Data

(60) Provisional application No. 62/234,182, filed on Sep. 29, 2015.

(51) Int. Cl.
| | | |
|---|---|---|
| *G01N 15/10* | (2006.01) | |
| *G01N 33/487* | (2006.01) | |
| *G01N 15/14* | (2006.01) | |
| *G01N 29/02* | (2006.01) | |
| *G01N 15/00* | (2006.01) | |

(52) U.S. Cl.
CPC ........... *G01N 33/487* (2013.01); *G01N 15/10* (2013.01); *G01N 15/1056* (2013.01); *G01N 15/1436* (2013.01); *G01N 15/1459* (2013.01); *G01N 15/1484* (2013.01); *G01N 29/022* (2013.01); *G01N 2015/0038* (2013.01); *G01N 2015/1043* (2013.01); *G01N 2015/1087* (2013.01); *G01N 2015/1454* (2013.01)

(58) Field of Classification Search
CPC ............... G01N 15/10; G01N 15/1056; G01N 15/1436; G01N 15/1459; G01N 15/1484
See application file for complete search history.

(56) References Cited

U.S. PATENT DOCUMENTS

| | | | |
|---|---|---|---|
| 8,232,584 B2 | 7/2012 | Lieber et al. | |
| 8,418,535 B2 | 4/2013 | Manalis et al. | |
| 2004/0233458 A1* | 11/2004 | Frick | G01D 5/268 356/480 |
| 2010/0231903 A1* | 9/2010 | Sumetsky | G01N 21/05 356/246 |
| 2016/0266110 A1* | 9/2016 | Ozdemir | G01N 15/1434 |
| 2017/0089881 A1* | 3/2017 | Bahl | G01N 33/487 |

OTHER PUBLICATIONS

Fumagalli, Laura, et al. "Label-free identification of single dielectric nanoparticles and viruses with ultraweak polarization forces." Nature materials11.9 (2012): 808-816.

(Continued)

*Primary Examiner* — Michael P Stafira
(74) *Attorney, Agent, or Firm* — Benesch, Friedlander, Coplan & Aronoff LLP

(57) ABSTRACT

A system and method includes nano opto-mechanical-fluidic resonators (nano-resonators), e.g., for identification of particles, e.g., single viruses and/or cells.

14 Claims, 10 Drawing Sheets

(56) References Cited

OTHER PUBLICATIONS

Wang, Shaopeng, et al. "Label-free imaging, detection, and mass measurement of single viruses by surface plasmon resonance." Proceedings of the National Academy of Sciences 107.37 (2010): 16028-16032.

Daaboul, G. G., et al. "High-throughput detection and sizing of individual low-index nanoparticles and viruses for pathogen identification." Nano letters 10.11 (2010): 4727-4731.

J. Lee, R. Chunara, W. Shen, K. Payer, K. Babcock, T. P. Burg, S.R. Manalis. Suspended microchannel resonators with piezoresistive sensors, Lab on a chip (2011).

* cited by examiner

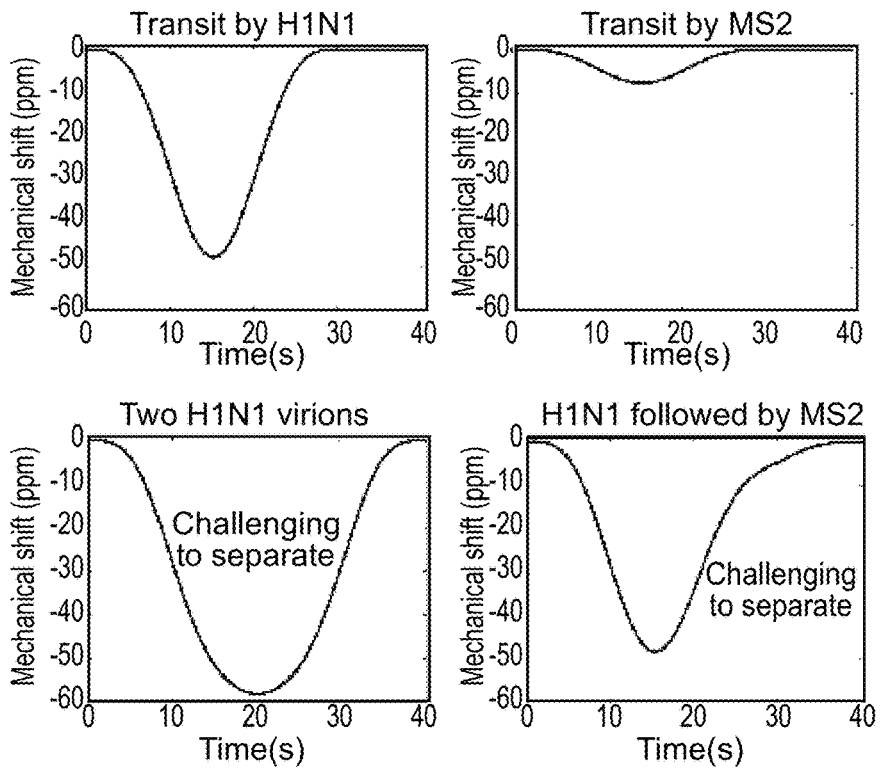
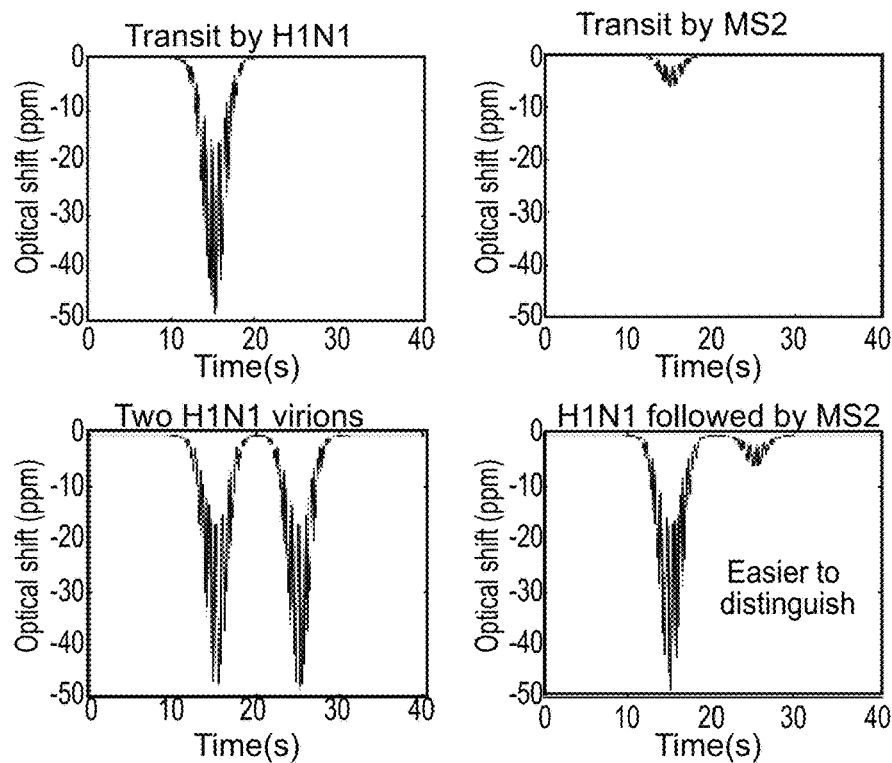
FIGURE 4

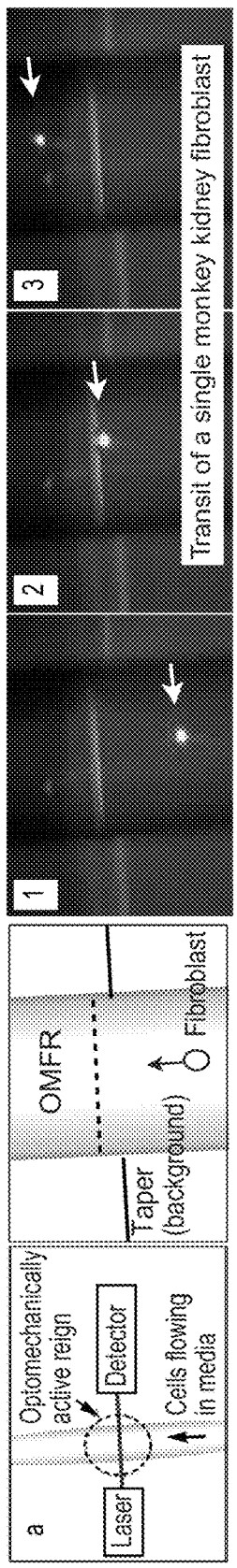
FIGURE 9A
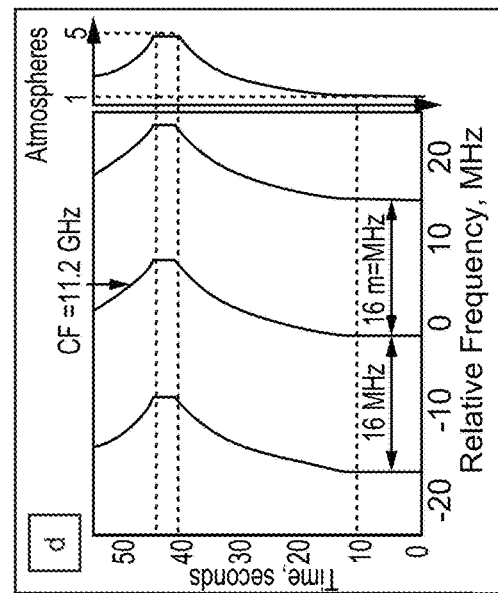
FIGURE 9D
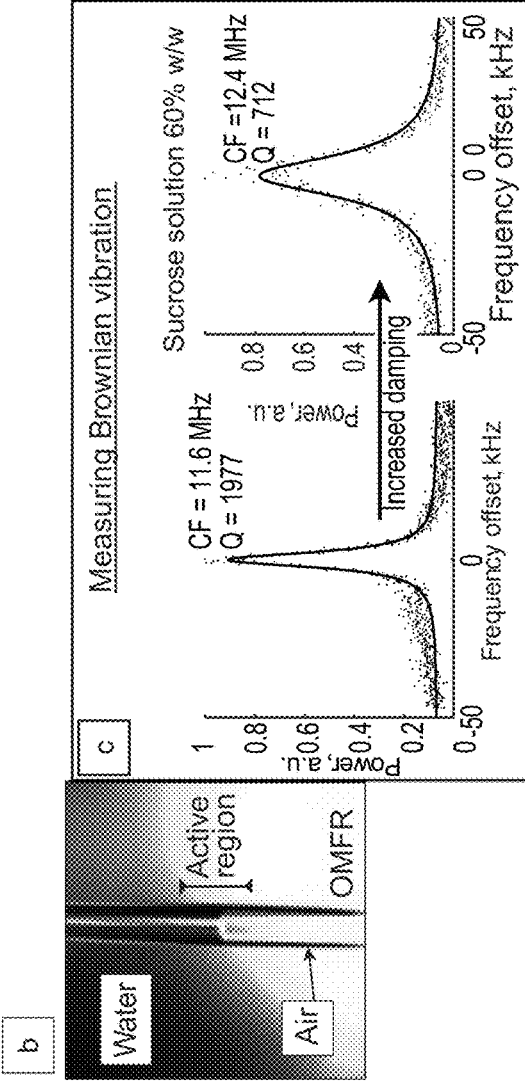
FIGURE 9C
FIGURE 9B

SYSTEM AND METHOD FOR NANO-OPTO-MECHANICAL-FLUIDIC SENSING OF PARTICLES

CROSS REFERENCE TO RELATED APPLICATION

This application claims the benefit of U.S. Provisional application Ser. No. 62/234,182, filed on Sep. 29, 2015, the disclosure of which is incorporated by reference herein in its entirety.

GOVERNMENT LICENSE RIGHTS

This invention was made with government support under grant number ECCS-1408539 awarded by the National Science Foundation (NSF). The government has certain rights in the invention.

BACKGROUND

Methods of non-specific, label-free single virus detection may provide limited information about individual virions. For instance, mechanical resonance methods primarily operate on the principle of mass-loading of a resonator and the associated frequency shift and have obtained yoctogram resolution. In this manner, the mass of a particle can be estimated with high resolution, but size and density are not obtainable without additional assumptions. Photonic methods, in contrast, rely on the shift of optical resonance frequency or optical mode splitting. This provides information on the polarizability, approximate size of a nanoparticle, but does not permit further identification.

BRIEF DESCRIPTION OF THE DRAWINGS

In association with the following detailed description, reference is made to the accompanying drawings, where like numerals in different figures can refer to the same element.

FIG. 4 includes graphs of example simulation of optical and mechanical sensing with properties of H1N1 Influenzavirus and MS2 virus.

FIG. 9A-D includes diagrams related to an example resonator device.

DETAILED DESCRIPTION

Figure 1A:
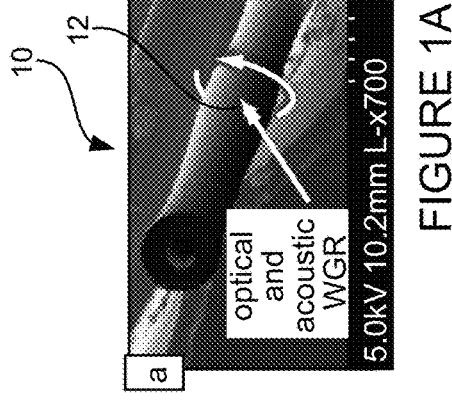
FIGS. 1A-D includes diagrams of an example resonator device, a test setup, and example measurements of liquid solutions.

Real-time identification of viral pathogens remains a pertinent, relevant, and pressing global scientific problem. The following systems and methods can provide increased measurement throughput, sensitivity, and/or particle identification (as opposed to detection), etc. by way of a nanofluidic optomechanical resonator. The systems and methods can provide simultaneous opto-mechanical label-free identification of particles, e.g., single virus particles and/or cells in various mixtures with high throughput. For example, having both optical and mechanical properties can shed much needed light on a single virion's size, mass density, and optical density (or polarizability), and can help narrow down the protein folding and virus structural properties and potentially enabling direct identification.

A nano-opto-mechano-fluidic resonator (nOMFR) can detect and identify single virus particles, not only based on their optical properties but also their mass and other mechanical properties. These simultaneous measurements eliminate large uncertainties and approximations that are employed with other current methods. Single virions can be sensed with simultaneous optomechanical measurements using the nOMFR. Models of optical as well as mechanical noise sources can be incorporated, along with the effects of radiation pressure and optomechanical back-action. A method of increasing the measurement throughput can enhance mechanical sensing, by using simultaneous optical information to spatiotemporally locate the nanoparticles. A rapid label-free identification of viruses can bring about advancements in human health diagnostics and therapeutics. Other types of particles can be identified, including but not limited to large molecules, deoxyribonucleic acid (DNA), and fragments from biological objects, e.g., exosomes, cell membranes, and small beads for sensing application. The systems and methods can help provide label-free identification, in contrast to the current methods of label-free detection. Current methods are not effective when multiple particles interact with a device and can only be operated at extremely low concentrations.

Viruses include nucleic acid sequences surrounded by protective coats (either protein or lipids or both). Several virion structural morphologies are known, including helical (rod shaped), prolate, icosahedral (almost spherical), or a hybrid structure as in the case of phages. The device need not distinguish the various shapes of viruses directly.

While two viruses might have similar length genomes (nucleic acid sequences), the manner in which the resulting protein sequence 'folds' determines the structural morphology and density of the virion. The density and optical polarizability (or refractive index) can thus be different for two viruses even when their mass is nearly the same. Similarly, while the mass of two viruses can be different, their optical activity can be similar due to the protein and lipid packing. The optical polarizability of a virion can be estimated based on the virus mass and the differential refractive index (dn/dc) of the virus in buffer solution. The error between optical response and mechanical response cannot permit the accurate identification of a virus without both pieces of information. Table 1 is an example list of virions of interest.

TABLE 1

Estimates of physical properties of virions of interest.

| Virus | Refractive index | Buoyant density (g/cm$^3$) | Diameter & shape (nm) |
|---|---|---|---|
| MS2 Coliphage | 1.570 | 1.4 | 23-30 (icosahedral) |
| T4 Coliphage | 1.368 | 1.5 | 100 (icos. complex) |
| C2 Bacteriophage | 1.367 | 1.46 | 110 (prolate complex) |
| R17 Bacteriophage | 1.431 | 1.49 | 26.6 (sph./hexagonal) |

TABLE 1-continued

Estimates of physical properties of virions of interest.

| Virus | Refractive index | Buoyant density (g/cm³) | Diameter & shape (nm) |
|---|---|---|---|
| PM2 Bacteriophage | 1.396 | 1.29 | 63 (icosahedral) |
| T7 Bacteriophage | 1.427 | 1.5 | 62 (complex) |
| Tobacco Mosaic Virus | 1.402 | 1.325 | 300 × 18 (helical rod) |
| H1N1 Influenza | 1.48 | 1.19 | 109 (icosahedral) |
| HIV | — | 1.042 | 120 (icosahedral) |
| Porcine Rotavirus (TLP) | — | 1.36-1.38 | 70-80 (icosahedral) |
| Porcine Rotavirus (DLP) | — | — | 60 (icosahedral) |
| Tomato spotted wilt virus | — | 1.21 | 70-90 (spherical) |
| Cucumber mosaic virus | — | 1.426 | 30 (sph./hexagonal) |
| Cauliflower mosaic virus | — | 1.37 | 50 (spherical) |
| Brome mosaic virus | — | 1.363 | 28 (icosahedral) |

High-Q whispering-gallery resonators (WGRs) can operate as single-particle detectors due to the high degree of light confinement they offer. This confinement occurs due to total internal reflection, and yet generates a slight evanescent optical field just outside the resonator, where photons are brought into repeated interactions with nanoparticles resting at the surface. Two methods of detection are dominant:

(1) Optical mode splitting relies on lifting the degeneracy between forward and backward propagating whispering-gallery modes (WGM) of the WGR. However, the mode splitting method does not offer sufficient resolution when the particle is significantly sub-wavelength in size. It is then only possible to estimate the particle polarizability through statistical measurements making single-particle sizing impractical.

(2) The Reactive Sensing Principle (RSP) is based on the shift of the optical mode due to the perturbation of effective refractive index applied by a nanoparticle. This method is reliable even when particles are deep sub-wavelength. The optical mode shift $\Delta\omega$ due to a particle can be generally written as:

$$\frac{\Delta\omega}{\omega} = -\frac{\Re[\Delta\alpha]E_o^2(\vec{r}_p)}{\int \varepsilon(\vec{r}) \cdot E_o^2(\vec{r})dV \text{ mode}} \bigg|_{point particle} \quad (1)$$

or $$\frac{\Delta\omega}{\omega} = -\frac{\int \Delta\varepsilon(\vec{r}_p) \cdot E_b(\vec{r}_p) \cdot E_a(r_p)*dV \text{ particle}}{\int \varepsilon(r) \cdot E_o^2(r)dV \text{ mode}} \bigg|_{over volume}$$

for a particle at position $\vec{r}_p$, having real part of excess polarizability $\Re[\Delta\alpha]$ or refractive index perturbation $\Delta\varepsilon$, and is independent of the specific optical resonator type. In the latter case, $E_b$ and $E_a$ are the mode fields before and after analyte insertion.

Since the detection of Influenza A using RSP in a WGR there has been a steady march of ever higher signal-to-noise ratio with bare resonators, reference interferometers, and gold nanoshells, reaching a 10 zeptogram (5 kDa) limit-of-detection (LOD) by employing plasmonic resonances. In all these methods, however, mass information is not directly measured but is only inferred through density assumptions. More recently, efforts have shifted towards the detection of single proteins.

Identification vs Detection: While it is generally believed that the size and the mass of the virion strongly correlate to the optical polarizability, there does exist an error (of several %) in these measurements that forbids true identification of the virion, and limits current methods to only performing detection. Thus, there is a need to independently and simultaneously measure the mass, size, and optical polarizability of viruses.

The principle of resonant mass sensing is based on the quartz crystal microbalance. Essentially, a perturbation in mass results in a perturbation in frequency $\Delta\Omega$, that can be expressed as:

$$\frac{\Delta\Omega}{\Omega} = -\left[\int \rho(\vec{r}_p) \cdot (y(\vec{r}_p)/y_{max})^2 dV \text{ particle}\right] / m_{eff, mode} \quad (2)$$

where $\vec{r}_p$ is the position of the particle, $y(\vec{r})$ is the spatial deflection function e.g. mode shape, $\Delta\rho$ is the replaced density from the particle, and m eff,mode is the effective mass of the resonant mode.

Previous in-vacuum experimental work focused on resonant mass spectroscopy of single cells, viruses, single molecules and proteins, and single atoms (generally referred to as particles) down to the yoctogram ($10^{-24}$ g) scale. Experiments in fluid submerged environments have been performed as well including the use of high-frequency high-order modes. To overcome the mechanical energy loss problem in fluid environments, resonators with integrated micro/nanochannels were developed and have recently demonstrated 0.85 attogram resolution. The ultimate limits of fluid-based mass detection have also been studied.

Throughput: While these devices exhibit good sensitivity, they can suffer from a throughput limitation where multiple particles cannot be easily distinguished as they interact with a device. Even so, bandwidth as high as about 1 kHz with about 27 attogram noise-equivalent resolution has been achieved. A multimode approach can also be used to resolve multiple particles. The systems and methods described below can utilize optical information to resolve this limitation in real time.

Photonic microresonators with high quality-factors enhance optical intensities (up to about $10^7$ times) through resonances known as whispering-gallery modes, magnifying the mechanical effects of light. Optical and mechanical resonant modes can thus be strongly-coupled through radiation pressure, photothermal pressure, gradient force, and electrostriction, resulting in high frequency MHz-GHz mechanical oscillations actuated by photons. These optomechanical vibrations have been employed for picogram scale and zeptogram scale measurements, but only in solid-state and in vacuum environments. The Opto-mechano-fluidic sensing described below can be used to work with arbitrary liquids.

Radiation pressure optomechanical oscillation originates in the following manner; photons carry linear momentum that is conserved; however, when they are compelled to travel a resonant path by the device momentum conservation requires the generation of reaction forces on the device. In tandem, a parametric instability is created as the optical resonance wavelength changes when the device is deformed by the optical force, causing the device to vibrate in one of its eigenmechanical 'breathing modes'. This also leads to a modulation of the light in the form of sidebands that can be measured using high-speed photodetectors.

FIG. 1 includes diagrams of an example resonator device 10, e.g., a optomechanofluidic resonator (OMFR). FIG. 1A is a diagram of an example silica glass resonator 10 with whispering-gallery resonator (WGR) region 12, in which, silica appears opaque in electron microscope images. FIG. 1B is an example resonator 10 mounted for experiment. FIG. 1C is an example setup where continuous-wave (CW) light source 14 is coupled to the resonator 10 from an adjacent tapered fiber 15 and the scattered light is analyzed. Sidebands formed due to optomechanical modulation can be detected by photodetector 16 and analyzed by an electrical spectrum analyzer 18. FIG. 1D is a graph of example sensing sucrose concentration with solution-loaded resonators 10 and radiation pressure actuated mechanical oscillation mode.

The OMFR 10 can be capable of simultaneous optical and mechanical measurements on arbitrary fluid-phase and gas-phase analytes. These devices can be employed in multiple modes of mechanical sensing for density, speed-of-sound measurements, and viscometry. The nanosensor can be achieved on opto-mechano-fluidic and OMFR principles.

Figure 1B:
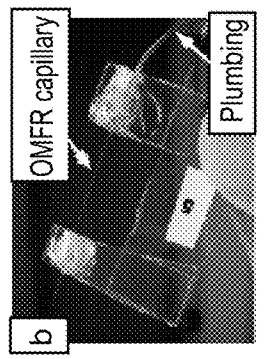
Figure 1D:
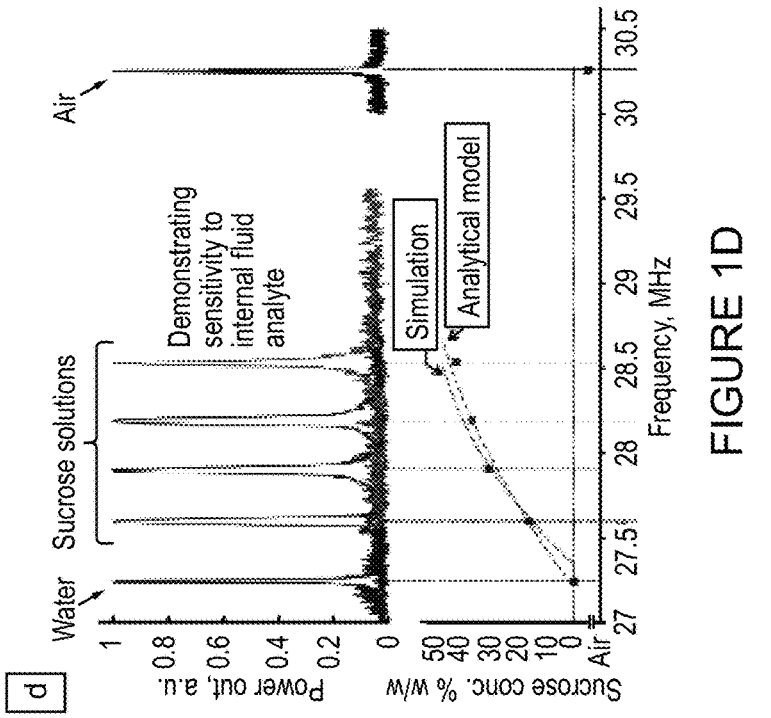
Figure 1C:
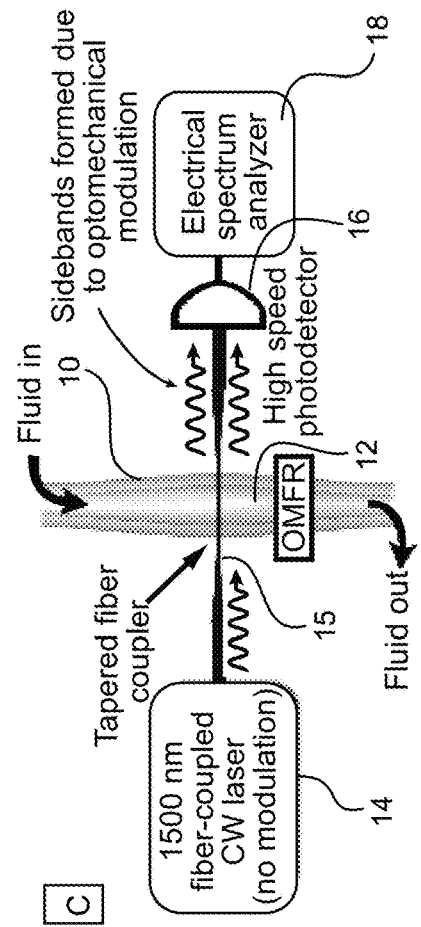

The resonator 10 can take the form of fused silica microcapillaries (FIGS. 1A and 1B). Ultra-high-Q fused-silica OMFR resonators 10 can be constructed with commercially purchased mm-scale capillaries using laser heating and drawing. By modulating the laser power during pulling, the device diameter is carefully controlled along its length. A light in and out of the optical whispering-gallery modes (WGMs) is coupled from a tunable fiber-coupled 1550 nm wavelength laser via a tapered optical fiber waveguide 15 (FIG. 1C). Optical WGMs and vibrational mechanical modes are then simultaneously confined in the regions of large diameter (FIG. 1A), enabling a high-degree of modal overlap.

Optical WGMs with quality factors up to about $10^8$, e.g. 100 million, can be measured on the resonators 10. Any mechanical modulation of the structure, for instance through thermal fluctuations, leads to an optical modulation that can be observed using heterodyne detection through photodetectors. In this manner, the mechanical vibration spectrum of the device can also be characterized. Multiple mechanical modes are observable, including breathing modes, wineglass modes, and whispering gallery modes. Optomechanics experiments with arbitrary fluid-phase materials have not been possible prior to the OMFR resonator 10 because fluid-submergence can affect light confinement (increased scattering and non-transparency in mixtures) as well as acoustic confinement (increased dissipation).

By increasing the optical power, the radiation pressure parametric instability or Stimulated Brillouin Scattering instability can be employed to opto-mechanically mechanical vibrations spanning several MHz up to 12 GHz, even with a dissipative fluid present within the device. The fluid participates in the optomechanical interaction since loading effects on the acoustic frequency are observed (FIG. 1d) when tested with water and sucrose solutions. For example, the pressure sensing can be performed using the optomechanical coupling in resonators 10, and the viscometry of arbitrary liquids demonstrated.

The resonator 10 can be used for particle, e.g., microparticle, measurement and single cells can exhibit a substantial perturbation of the mechanical mode without affecting the optical performance. To achieve this, a computational capability for fluid-structure interaction within resonators 10 is described below. A multi-mode sensing principle is also described for simultaneously extracting density and speed of sound of the internal analyte deterministically.

With regards to single virus detection, there can be a few shortcomings of microcapillary based resonator 10, e.g., their large mass. The mechanical vibrational modes in capillary resonators 10 have effective masses in the microgram-nanogram range. As a result, small viral particles with masses in the 500 attogram range cannot create measurable perturbation of the vibrational mode. The presence and location of a particle can, in principle, be measured by a reactive shift of the optical modes of the resonator 10. This interaction takes place by the particle perturbing the evanescent optical field on the inside of the resonator 10. However, these modes are not well localized in bottle-shaped resonators. While a technique to identify latitudinal particle location on spherical WGRs has been recently demonstrated, this does not convey information about longitude. Further, prior knowledge or identification of the optical mode can be needed, but is challenging in such overmoded WGRs. Potential solutions can include nanomechanical resonators 20 (as opposed to micromechanical resonators 10), with well-defined tightly-localized photonic modes that provide three dimensional particle location information.

Whispering gallery modes (WGMs) are resonant modes of a circular device that are created when an integer (M) number of periods of the traveling wave (optical or acoustic as the case may be) fit along the device circumference (2πR). This results in constructive interference and resonant enhancement of the wave amplitude within the device. The resonant wavelength is then $\lambda_o=2\pi R/M$.

Fabrication: a high speed and low cost OMFR resonators 10 (FIGS. 1A and B) can be fabricated with a fused-silica glass capillary preform that is pulled lengthwise while being heated with infrared wavelength lasers. By modulating the laser power during pulling, the device diameter can be controlled along its length. Optical WGMs, acoustic WGMs. and acoustic breathing modes are simultaneously well-confined in the regions of large diameter, enabling a high-degree of opto-mechanical modal overlap. Multiple such resonators can be built on a single capillary. This manufacturing process has previously been developed in the context of optofluidics. Fabrication of the device can take only a few minutes, which is an advantage for fast deployment.

Optomechanics examples: couple light in and out of the optical WGMs from a tunable fiber-coupled 1550 nm wavelength laser via a tapered optical fiber waveguide 15 (FIG. 1C). Optical WGMs with quality factors (which describe the photon loss rate) up to $10^8$ are measured. This means that a 1550 nm photon in a 100 micron diameter resonator can make about $10^6$ round trips of the device (e.g. resonance), which translates to a total optical intensity enhancement by the same factor (1 mW input can translate to 1000 W of circulating optical power). Such resonant enhancement of light allows the magnification of mechanical forces as well. Acoustic modes are observed via the light that is scattered from them, by way of temporal interference with the pump laser measured on a photodetector.

Radiation Pressure (RP) Optomechanics with Mechanical Breathing Modes

Figure 7:
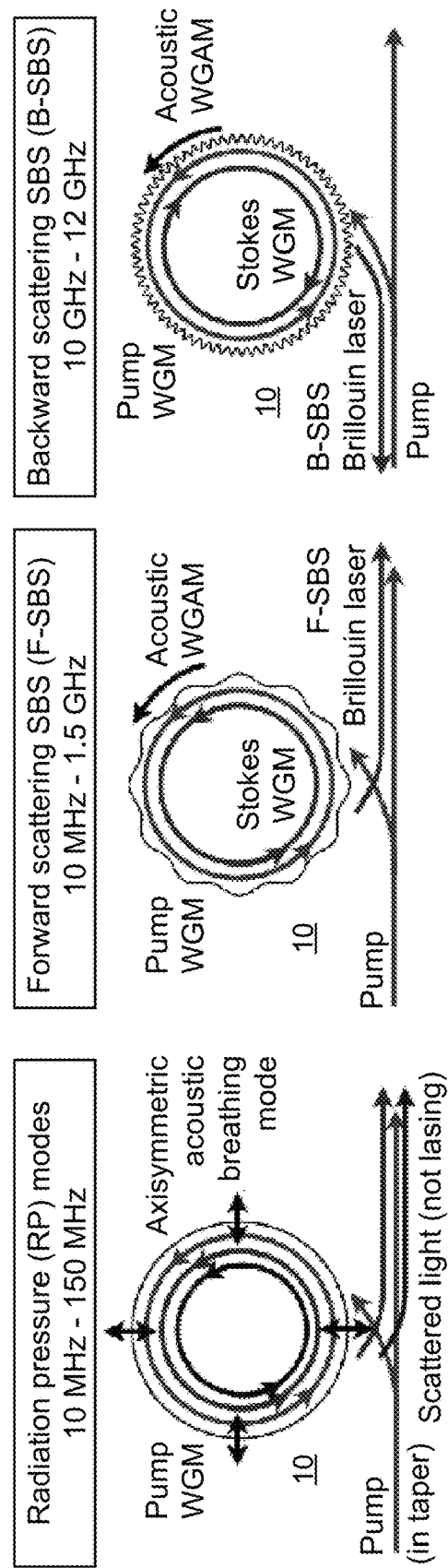
FIG. 7 are examples of optomechanical actuation in fluid-filled resonator devices.

The actuation of "breathing" vibrational modes (axisymmetric) can be demonstrated by centrifugal radiation pressure. Radiation pressure optomechanical oscillation originates in the following manner; photons carry linear momentum that is conserved; however, they are compelled to travel a circular WGM path by the device, which can only be resolved when a centripetal acceleration acts on the photons and a corresponding centrifugal force is generated on the device. In tandem, a parametric instability is created as the optical WGM resonance wavelength changes when the device is deformed by the optical force, causing the device to vibrate in one of its eigenmechanical 'breathing modes'. The morphology of the optical and acoustic modes is illustrated in FIG. 7. The device can achieve optomechanical actuation of these RP modes at frequencies ranging from 10 MHz-150 MHz even with a dissipative fluid present within the device. The fluid participates in the optomechanical interaction since loading effects on the acoustic frequency are observed (FIG. 1D) when tested with water and sucrose solutions.

Figure 2:
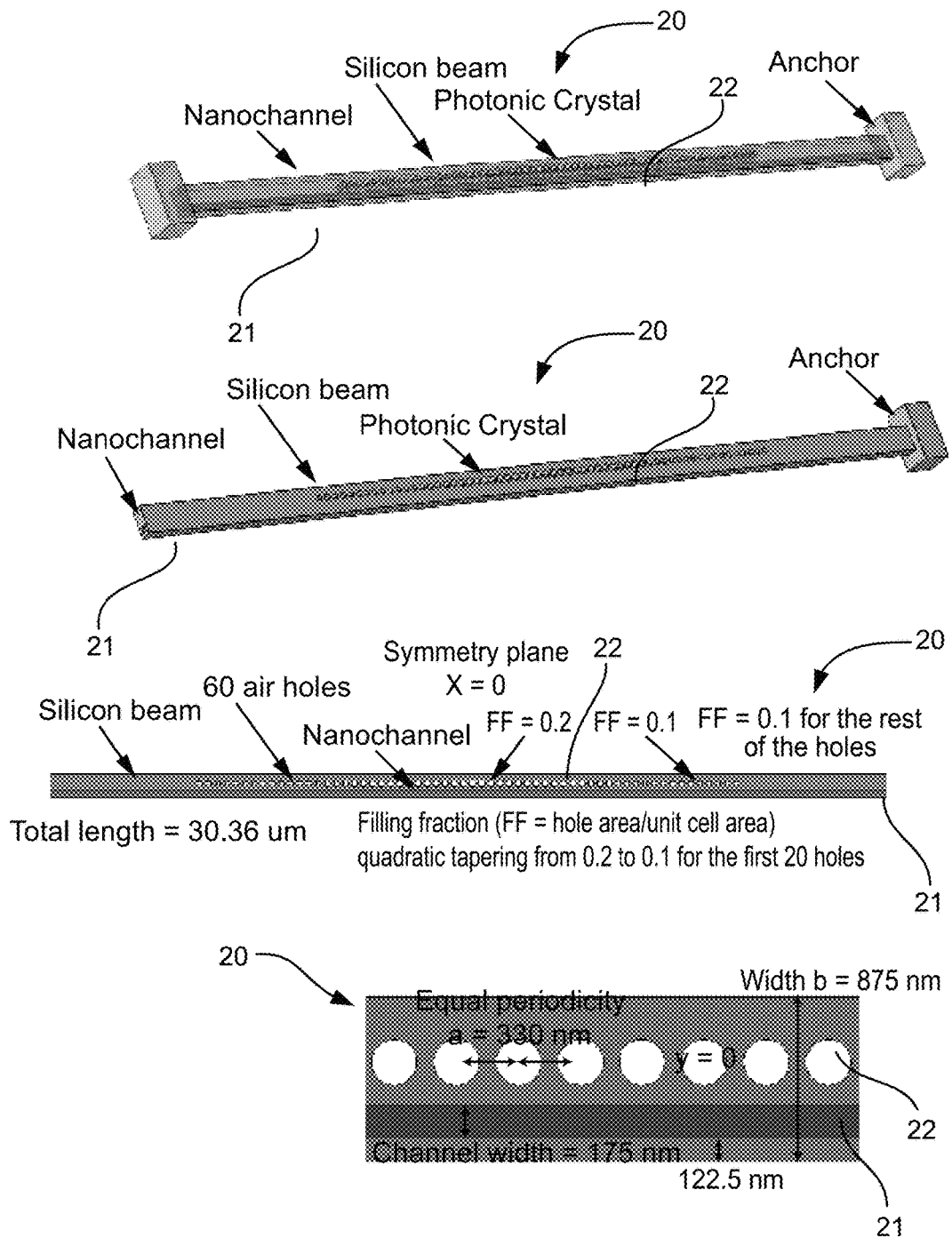
FIG. 2 is a diagram of an example nano-resonator device.

FIG. 2 is a diagram of an example nano-resonator device 20, e.g., nano-optomechanofluidic resonator (nOMFR). The nano-resonator 20 is a fixed-fixed beam resonator with an integrated nanochannel 21 and integrated photonic crystal, e.g., by drilling holes 22 in a determined substrate. Sixty holes are shown, but other amounts of holes may be used. The nano-resonator 20 simultaneously confines both light and sound. The holes 22 are positioned adjacent the nanochannel 21 to perform as optical position sensitive ruler. Example device dimensions are indicated in FIG. 2. In some embodiments, the device mass of the nano-resonator 20 is <10 pg (picograms) as a result of which sub-femtogram detection resolution is achievable. The nanochannel 21 passes through the photonic crystal resonator and the optical field is shared (see FIG. 2) to obtain direct optical detection of nanoparticles. The substrate and supporting microfluidics are not illustrated.

A fixed-fixed beam nanomechanical resonator (30.3 um length, 750 nm thickness) can contain a (175 nm) nanofluidic channel 21 through half its width, while supporting a photonic crystal (PC) optical resonator through the remainder of its width. The nano-resonator 20 is illustrated in FIG. 2 and the calculated modes are described in FIG. 3. The photonic crystal resonator can be employed for high resolution photonic readout of the picometer-scale mechanical deflections caused by thermal phonon occupation of the vibrational modes of the beam. In this regard, unlike the optomechanical crystal devices and the suspended microchannel resonators (SMRs) that have been built previously, the nano-resonators 20 can have an integrated miniaturized photonic sensor as opposed to a free space optical detection setup.

Optical detection with WGRs can have the advantage of high Q-factors. PC resonators have lower Q, but compensate by confining maximum optical energy in an extremely small (order-of-wavelength) mode volume. Thus, the fractional perturbation of the optical mode caused by the presence of a single particle in the case of PC resonators can be extremely large. In addition, PC resonators enable the three-dimensional localization of a particle, as opposed to only knowing latitude in the case of WGRs.

FIGS. 3A-B includes diagrams and graph of example mechanical and optical sensing modes. The example nano-resonator 20 can be designed to have (a) vibrational modes in the 10 MHz range, and (b) photonic modes in the 1.55 um (telecom) wavelength range (165 THz/1.8 um mode shown). The vibrational modes permit direct mass sensing of analytes within the nanochannel 21 in a manner similar to previous work. The photonic modes provide higher resolution, position, size, and polarization information on the particle. The nanochannel 21 provides good localization of the nanoparticles within the optical field. Many other modes of this structure can exist.

Figure 3:
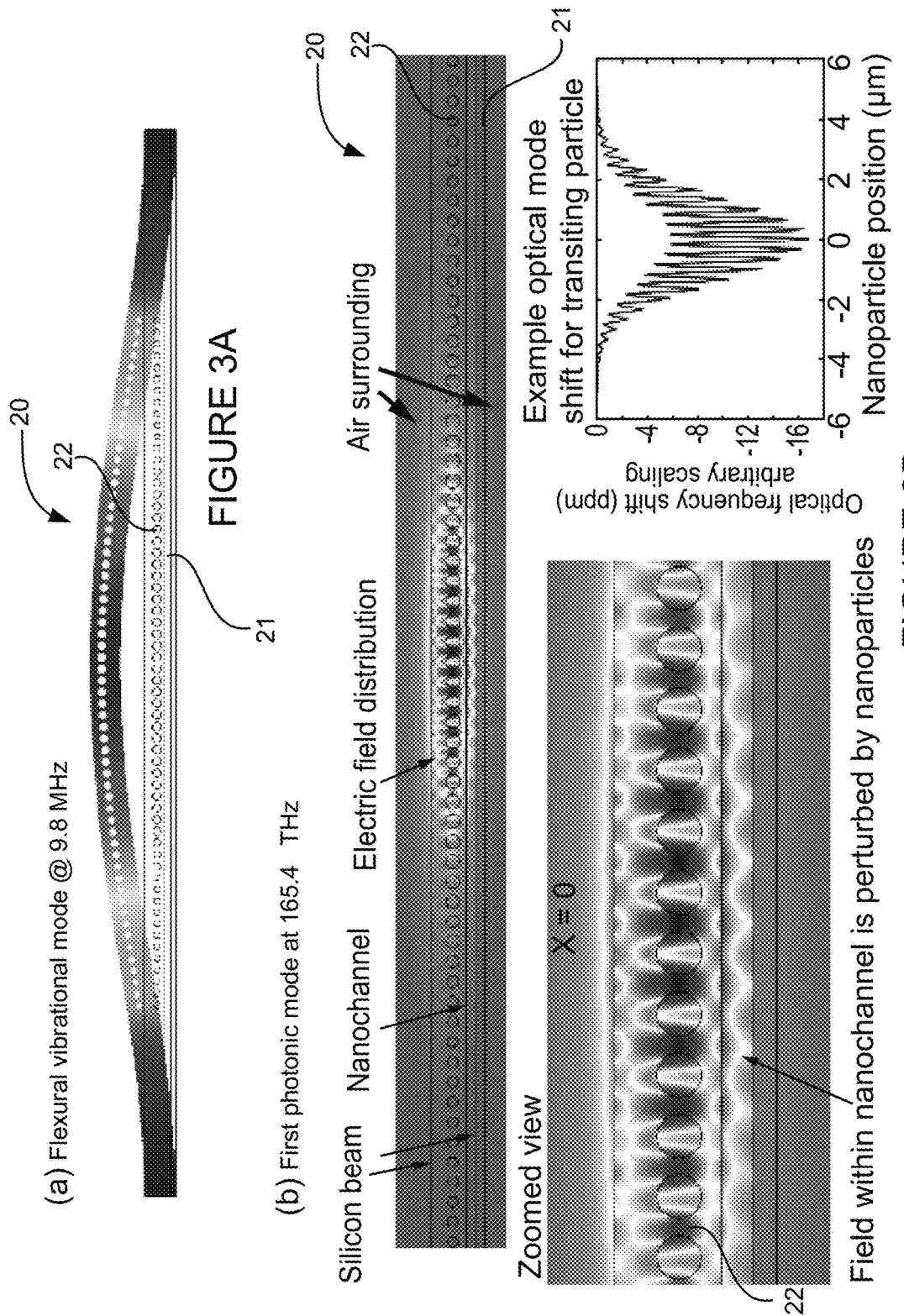
FIGS. 3A-B includes diagrams and graph of example mechanical and optical sensing modes.

For the example device, 2D simulations can be performed to predict the sensitivity to individual virions. The basic principles of mass loading are able to theoretically predict the fractional mechanical frequency perturbation of the resonator as a virion passes through the nanochannel 21 (FIG. 4). Similarly, the generalized reactive sensing equations (Eqn. 1) can be used to computationally analyze how a single virion perturbs the optical mode of the structure as it passes through the nanochannel 21 (FIG. 3). In FIG. 4, the transits of multiple closely spaced virions can be optically resolved, while a mechanical-only measurement is unable to distinguish them. However, mechanical measurements are used for extracting mass information from the virion.

Mechanical mass sensing: The nanofluidic channel 21 can be infused with a carrier fluid (selected based on the virion). When virions transit the resonator through the nanofluidic channel 21, the mass of the resonator beam can be perturbed. Example 2-dimensional simulations predict 10's of ppm frequency shifts in the case of Influenzavirus H1N1 (FIG. 4). This may be an overestimate due to the 2D simulation, so calculations can be revised with a full 3D simulation in Task 1 (see later). Since mechanical frequency shifts in the ppb range can easily be resolved, mechanical sensing can be adequately achieved a high degree of confidence.

FIG. 4 includes graphs of example simulation of optical and mechanical sensing with properties of H1N1 Influenzavirus (800 attograms, hydrated) and MS2 virus (20 attograms, hydrated), of very different size, mass, optical properties. At this level of magnification, the optical 'fringes' appear as a blur.

Photonic sensing: The photonic resonator integrated in the beam resonator can be designed such that a significant evanescent optical field exists within the nanofluidic channel 21 (FIG. 3B). This optical field can thus be perturbed by nanoparticles transiting the device. Note that the optical modes are of extremely high order (showing lots of antinodes) compared against the mechanical modes, and as a result much better position information can be obtained. Further, the mode is a standing wave (as opposed to a traveling wave in the WGR case) so localization in all three dimensions can be achieved. It can be estimated that the fractional perturbation of the optical mode can also be in the 10's of ppm (e.g. picometer shifts), which can be revised with a 3D simulation, in the case of Influenzavirus. Optical mode perturbations as small as a 10 femtometers can be measured in WGR nanoparticle sensing experiments.

Task 1: Fundamental Limits of Sensing

Computational and analytical models can be used for both the mechanical and optical response of the example device, which can be iteratively employed to improve the design. Noise is an important participant when operating at the limit of sensitivity. The various noise contributions present in these devices can be analyzed to predict and optimize the signal-to-noise ratio. These calculations can help more accurately determine the limit-of-detection (LOD) with the nano-resonators 20, and can assist with iterative design improvements prior to fabrication.

Task 2: Example Nano-Resonator 20 Device Fabrication

The example nano-resonators 20 can be fabricated based on designs from Task 1. Here we propose an example fabrication method for producing nano-resonators 20. Other methods to produce nano-resonators 20 may also be used. Silicon nitride structures can be built using a polysilicon sacrificial layer to describe the nanochannel 21. The process can be modified to construct structures with space adjacent to the nanochannel 21 for patterning a photonic crystal resonator. The alternative combination of silicon (device) and silicon dioxide (sacrificial) materials is also a candidate for device fabrication. The final materials choice can be made based on of various noise sources and optimizations from Task 1. Due to the likely complexity of the process, an optical waveguide is not integrated in the first generation device and instead tapered optical fiber 15 can be used during testing (Tasks 3-5).

A supporting microfluidic infrastructure can be prepared in addition to the nano-resonator. Bypass channels 40 and other fluid routing channels can be co-fabricated with the device on the same chip. While lithography and fabrication in the sub-micron regime can be challenging, there is experience with these dimension scales. Further, practical nanochannels 21 as small as 45 nm width have been fabricated in the past, using interference lithography followed by material deposition for achieving smaller diameters. Here, the intent need not reach the <50 nm size regime. Lithography in the >100 nm regime is achieved through electron-beam patterning.

Figure 5:
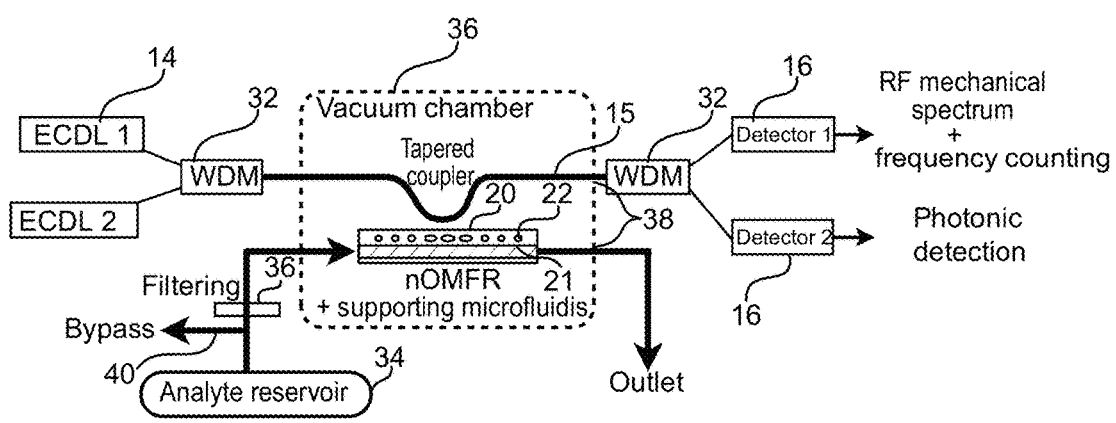
FIG. 5 is a block diagram of an example system for nano-resonator device.

FIG. 5 is a block diagram of an example system for nano-resonators 20. Each External Cavity Diode Laser (ECDL), or other light source 14, monitors optical modes and different points in the spectrum. High speed photodetectors 16 are able to resolve the mechanical modes, measured through the optical sidebands.

Task 3: Characterization and Testing

Example testing of the nano-resonators 20 can be performed in a vacuum chamber 36 equipped with fluidic, optical, and electronic feedthroughs 38. This allows to control both pressure and temperature, thereby eliminating or reducing several noise mechanisms. An example setup is in FIG. 5. Analytes, or other particles to be sampled, can be fed to the nano-resonator 20 from an analyte reservoir 34. The analytes can be filtered by filter 36 before entering the nano-resonator 20.

Light can be coupled to the optical resonant modes of the device through a tapered optical fiber coupler 15 due to its extremely high coupling efficiency. The device can be integrated with waveguides and grating couplers to minimize vibration issues and to improve robustness of the optical coupling method. A fiber-coupled telecom laser (1520-1570 nm) or other light source 14 can be employed to probe the optical modes. By monitoring the mechanically-modulated light spectrum at the opposite end of the fiber 15, the mechanical vibrational spectrum can be measured. In addition, wavelength division multiplexers (WDMs) 32 can be employed to simultaneously monitor at least two optical modes. Fiber WDMs are inexpensive and are readily available from Thorlabs. This multimode measurement can allow to obtain significantly higher resolution information on the particle position and size by borrowing a recent concept from WGRs. High frequency photodetectors can be used to simultaneously monitor the radio-frequency spectrum of multiple mechanical vibrational modes in the MHz range.

Figure 6:
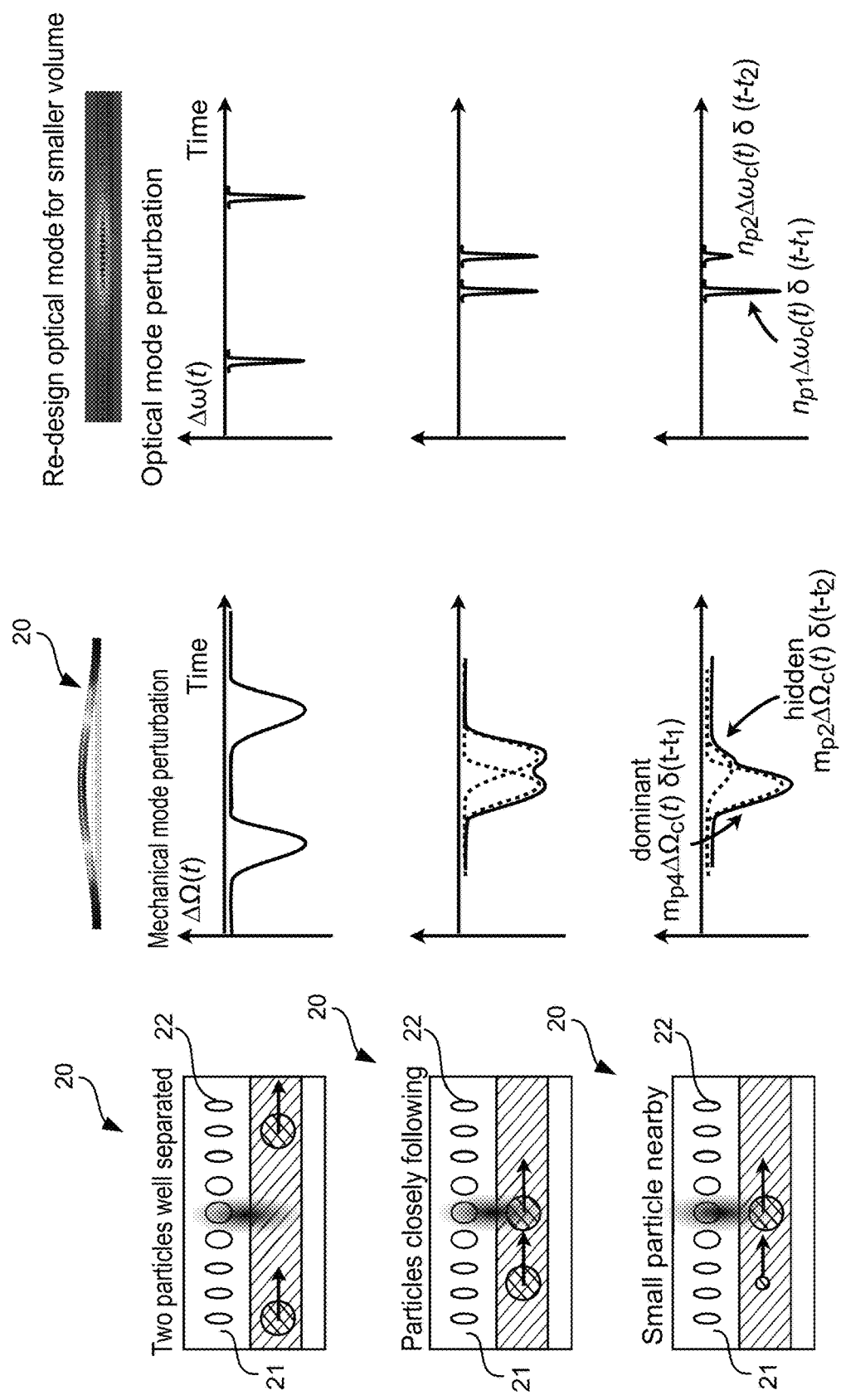
FIG. 6 are diagrams and graphs of example resolving multiparticle signals.

FIG. 6 are diagrams and graphs of example resolving multiparticle signals. The central fringe can be directly read from the optical method to obtain the particle transit times. Data extraction post-processing from the mechanical signal in the presence of background noise can be improved and real-time high throughput mechanical sensing can be achieved.

Task 4: Mechanical Sensing Throughput Enhancement

If too many particles pass through the nanochannel 21 at the same time, the vibrational signatures can blend together and become non-discernable (FIG. 4 and FIG. 6). The traditional method to address this is severe dilution of the analyte such that this situation does not occur. However, that leads to a dramatically reduced throughput for sensing. An example throughput enhancement technique is explained mathematically below, and diagrammatically in FIG. 6. The time-dependent mechanical frequency shift $\Delta\Omega(t)$ from a series of particles flowing through the nano-resonator 20 can be expressed as a function of the $i^{th}$ particle mass $m_{pi}$, its transit time $t_i$ expressed through a Dirac delta function, convolved (*) with the characteristic perturbation from a single isolated particle $\Delta\Omega_c(t)$.

$$\Delta\Omega(t) = \Delta\Omega_c(t) * \sum_i m_{pi}\delta(t-t_i) \quad (3)$$

Determining the transits of two closely spaced particles becomes difficult, especially without extensive data processing, since the characteristic mechanical frequency perturbation function $\Delta\Omega_c(t)$ typically has a wide spread over time (FIG. 4 and FIG. 6). The photonic response can similarly be written as:

$$\Delta\omega(t) = \Delta\omega_c(t) * \sum_i n_{pi}\delta(t-t_i) \quad (4)$$

where $n_{pi}$ is the refractive index (or alternatively, polarizability if expressed differently) of the particle. Note, however, that with suitable photonic crystal design the characteristic optical perturbation function $\Delta\omega_c(t)$ can be made much narrower than its mechanical counterpart. As a result, when the optical perturbation experimental data is normalized (with a signum function for instance) to remove the effects of $n_{pi}$ it can directly be employed to identify the particle location $\delta(t-t_i)$. Knowledge of particle timing $t_i$ can significantly reduce the processing required for deconvolving $m_{pi}$ out of Eqn. 3. A real-time sensor can then be built, eliminating the need for guesswork or elaborate curve fitting.

Task 5: Virus Identification Experiments

An objective is to identify different viruses from mixtures. After Tasks 1-3, simultaneous extraction of the optical and mass information can be demonstrated from a single-pass measurement of a single virion. By doing so, the particle populations can be mapped on a two-dimensional plot (similar to a flow cytometry) and identify sub-populations. With suitable model systems and fluorescent tagging, the sensor can be calibrated and a database of virus information can be produced. Polystyrene nanobeads can also be employed.

Several noise sources can limit detection resolution and can be considered, including photon shot noise, particle shot noise, optical thermorefractive noise, momentum exchange noise, and thermomechanical fluctuations.

Thermorefractive noise and thermoelastic noise appear due to the fundamental temperature fluctuations within the device material. The coefficient of thermal refraction (dn/dT) operating on these fluctuations leads to thermorefractive noise. The coefficient of thermal expansion creates thermoelastic noise on both the photon modes and the mechanical resonance modes. In the case of photon modes, the thermoelastic contribution is generally negligible. Mechanical frequency sensitivity to these fluctuations can be reduced by increasing the thermal time constant of the device. In addition, these thermal fluctuations cause perturbation of the speed of sound in the material, which also induces a mechanical frequency fluctuation. Thermomechanical noise arises from the thermally driven motion of the nanomechanical device, which are also a consequence of the fluctuation-dissipation theorem. This can be controlled by operating the device at lower temperature, or increasing the device mechanical Q-factor in a vacuum environment.

Photon shot noise (PSN) arises due to the independent randomized arrival times of photons at the optical detector. PSN can be reduced by increasing the source laser power. In the limit of large input power, however, the photons can impart sufficient momentum to the structure so as to create a perturbation of the mechanical mode, which is called radiation pressure shot noise (RPSN) and creates "measurement back-action". The transition between PSN and RPSN is commonly termed as the standard quantum limit, as it describes the best measurement resolution achievable. In the nano-resonator 20, a low RPSN can be anticipated since a large optomechanical coupling is not expected, which can allow to turn up the optical power for reducing PSN.

Momentum exchange noise is expected to arise from external gas molecules imparting momentum kicks to the resonator, and adsorption-desorption noise appears from the mass loading due to gas molecules present in the resonator environment. Both these noise sources can be eliminated/minimized by operating the device in a vacuum chamber.

Impact to human health and virus sensing: the nano-resonator 20 can provide a new degree of freedom in single virus sensing by generating simultaneous optical and mechanical measurements. This new degree of freedom opens up a new two-dimensional space for discerning and potentially identifying single virions, and eliminates uncertainties and approximations that are currently applied. Thus, this is a capability can transform current methods of label-free nanoparticle sensing which operate only in one-dimensional information. More broadly, a new method for throughput enhancement is developed for flow-through mechanical resonance sensing which can be applied to other micro/nano-channel sensors. Such devices can be deployed in the field for the rapid label-free identification of viral pathogens, and for generating a swift response by healthcare authorities. In pharmacological studies, these devices can assist in rapid drug discovery.

Shorter wavelengths (for instance, 780 nm as opposed to 1550 nm) can offer a better limit of detection for the optical sensing in the system. However, short wavelengths can require correspondingly smaller lithographic features for the photonic crystal structure. To simplify the first demonstration of this example sensor, the nano-resonator 20 device can be operated near 1550 nm wavelength, which significantly reduces the fabrication effort and allows to use existing telecom wavelength equipment. Other wavelengths can be used to operate the nano-resonator 20, e.g., in the 780 nm regime. Additionally, nanochannel 21 functionalization through antibodies can be used in to more specifically identify certain viruses.

FIG. 7 are examples of optomechanical actuation in fluid-filled resonators 10. The pump laser is a sub-milliwatt continuous-wave source and is not modulated in any way. The mechanical vibrations are excited by parametric instabilities. Brillouin optomechanics can be performed with whispering gallery acoustic modes (WGAMs) using stimulated Brillouin scattering (SBS) which is an acousto-optical amplification process involving hypersonic bulk-acoustic waves in a material.

FIGS. 8A-F is graphs of example measured WGAM modes and their example computationally modeled deformation profiles. The spectra shown are the temporal beating of the pump laser and the scattered Stokes laser as detected by a photodetector, which is a measure of the acoustic mode.

Figure 8C:
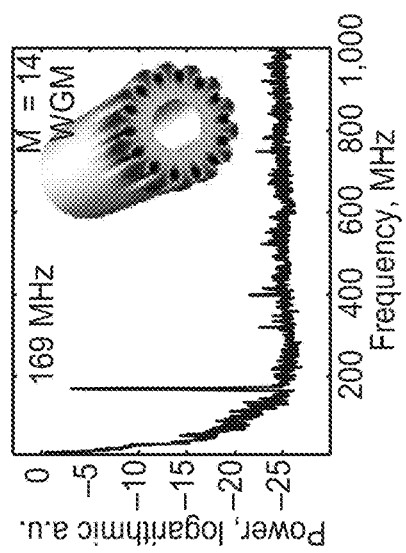
FIG. 8A-G is graphs of example measured vibrational modes of fluid-filled resonator devices (WGAM is whispering gallery acoustic mode) and their computationally modeled deformation profiles.
Figure 8B:
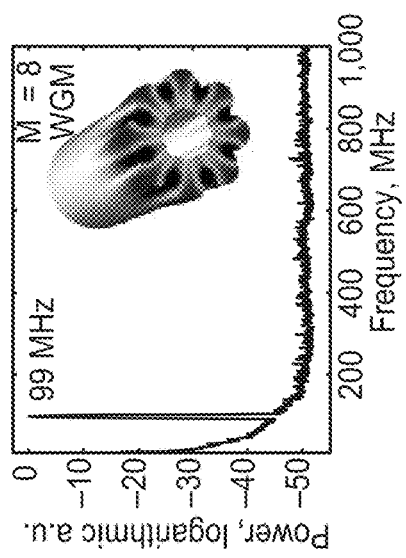
Figure 8A:
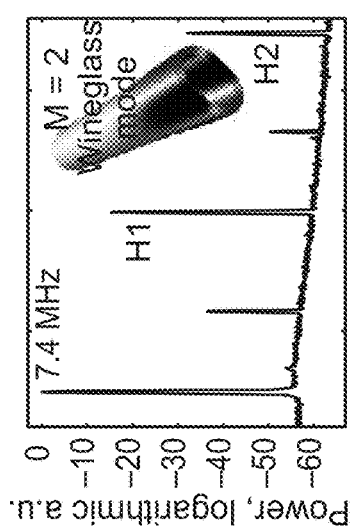
Figure 8F:
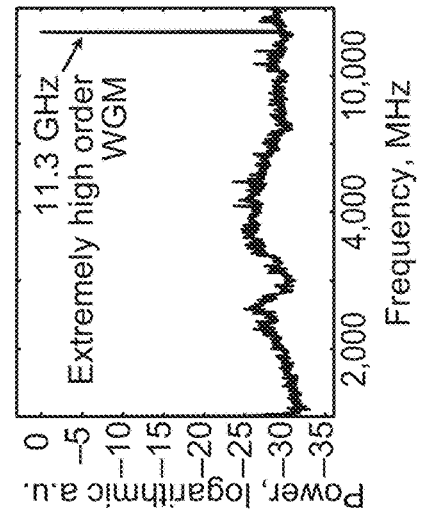
Figure 8E:
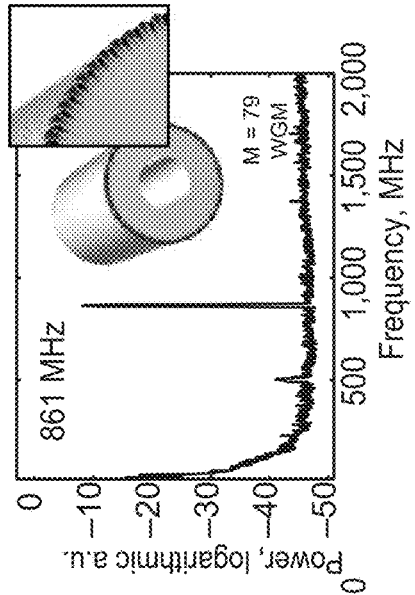
Figure 8D:
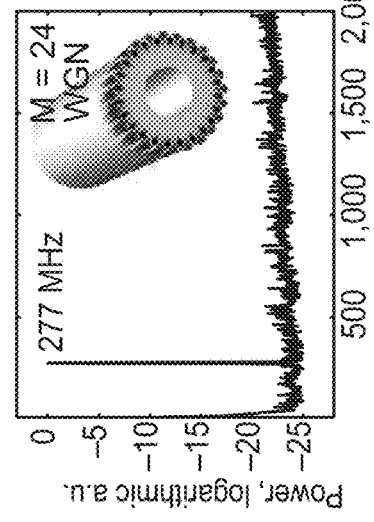
Figure 8G:
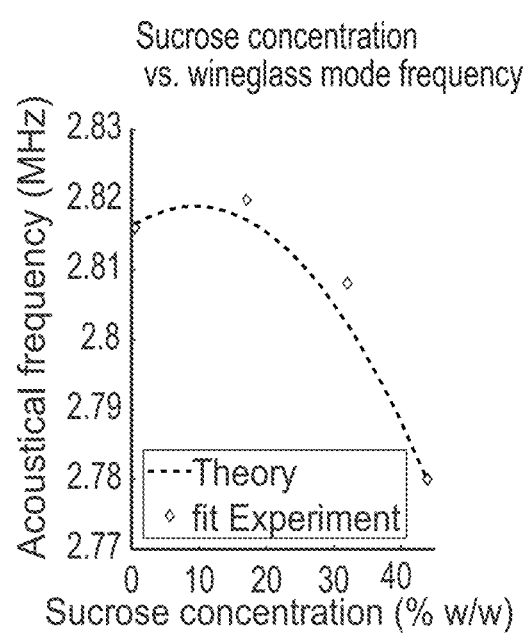

FIG. 8G Demonstrates sensitivity to varying sucrose solutions, which need better models. The long phonon lifetimes in this low-frequency regime cause the mechanical mode to exhibit lasing behavior, in essence forming the acoustical analogue of optical lasers.

FIGS. 9A-D includes diagrams related to an example resonator 10. FIG. 9A illustrates an optomechanical example with a single CV-1 monkey kidney fibroblast cell flowing in media. In FIG. 9B, testing size of the acoustic modes is illustrated with loading from a controlled water meniscus inside. In FIG. 9C, effects of fluid viscosity are measurable in Brownian mechanical motion, with 12 MHz modes. In FIG. 9D, resonator 10 aerostatic tuning is illustrated with simultaneous 11 GHz SBS and 16 MHz RP modes.

Weighing single cells with optomechanics: individual cells can be flowed through resonators 10 (FIG. 9A). As the cells flow past the active region, the mechanical mode can be perturbed. It has been previously noted that optoelectromechanical regenerative amplification can reach $10^{-17}$ g resolution, limited by thermomechanical fluctuations.

Aerostatic pressure tuning and resolving taper coupling challenges: Tapered fiber 15 coupling is sensitive to small changes in the device-taper distance. This is a concern when working with deformable shell-type resonators (e.g., resonators 10) under pressure-driven flow. The taper is in contact with the resonator which eliminates the ambient vibration-sensitivity of the device. The taper contact causes a quenching of the Q-factors of the optical modes. In FIG. 9D the RP-driven and SBS-driven oscillations can be sustained simultaneously, and are able to measure pressure, in spite of this Q reduction. Indeed, pressure tuning provides a method to intentionally modify optical and acoustic modes for 'frequency-on-demand' MHz-GHz spectrum coverage.

Optomechanical viscometer: The linewidth of Brownian mechanical vibrations of the breathing mode of the resonators 10 is representative of the damping loss due to a fluid (associated with viscosity). The Brownian mechanical motion can be observed (FIG. 9C) and its variation (indicating change in damping) when different fluids are loaded in the device, thus proving the sensitivity to viscosity and femtometer-scale mechanical motion.

The systems, methods, devices, and logic described above may be implemented in many different ways in many different combinations of hardware, software or both hardware and software. For example, all or parts of the system may include circuitry in a controller, a microprocessor, or an application specified integrated circuit (ASIC), or may be implemented with discrete logic or components, or a combination of other types of analog or digital circuitry, combined on a single integrated circuit or distributed among multiple integrated circuits.

Many modifications and other embodiments set forth herein can come to mind to one skilled in the art having the benefit of the teachings presented in the foregoing descriptions and the associated drawings. Although specified terms are employed herein, they are used in a generic and descriptive sense only and not for purposes of limitation.

The invention claimed is:
1. A system comprising:
a resonator, the resonator comprising a beam and a nanochannel passing through the beam, the resonator further comprising a photonic crystal positioned in the beam and adjacent the nanochannel, where the nanochannel contains a liquid, and where the liquid contains particles to be sensed, where the photonic crystal confines light in a photonic mode, the beam confines sound in a mechanical mode, and motion within the mechanical mode modifies the photonic mode;

an optical fiber coupled adjacently to the resonator, the optical fiber to guide a light wave past the resonator, and a detector positioned at an output of the optical fiber, where the detector detects changes in the light wave to detect a mechanical property of the particles based on the confined sound and a position of the particles based on the confined light.

2. The system of claim 1, where the detection by the detector is label free.

3. The system of claim 1, where the detector simultaneously detects a size and mass of the particles.

4. The system of claim 1, where the particles comprise at least one of viruses, large molecules, DNA and fragments from biological objects.

5. The system of claim 1, where the nanochannel comprises half a width of the beam and the photonic crystal comprises half a width of the beam.

6. The system of claim 1, further including a mixture to suspend the particles.

7. The system of claim 1, where the particles comprise cells.

8. The system of claim 1, where the particles comprise at least one of micro-particles and nanoparticles.

9. The system of claim 1, where the position sensing reduces a uncertainty from the mechanical property sensing.

10. The system of claim 1, where the optical fiber is tapered.

11. The system of claim 1, further comprising wavelength division multiplexers positioned on ends of the optical fiber.

12. The system of claim 1, further comprising a light source connected with one end of the optical fiber and the detector coupled with another end of the optical fiber.

13. The system of claim 12, where the light source comprises a laser.

14. The system of claim 1, where the photonic crystal comprises a plurality of holes which convey where the particle is located within the nanochannel.

* * * * *